(12) United States Patent
Berner et al.

(10) Patent No.: US 6,488,962 B1
(45) Date of Patent: Dec. 3, 2002

(54) TABLET SHAPES TO ENHANCE GASTRIC RETENTION OF SWELLABLE CONTROLLED-RELEASE ORAL DOSAGE FORMS

(75) Inventors: Bret Berner, El Granada, CA (US); Jenny Louie-Helm, Union City, CA (US)

(73) Assignee: DepoMed, Inc., Menlo Park, CA (US)

( * ) Notice: Subject to any disclaimer, the term of this patent is extended or adjusted under 35 U.S.C. 154(b) by 0 days.

(21) Appl. No.: 09/598,061

(22) Filed: Jun. 20, 2000

(51) Int. Cl.$^7$ .............................. A61K 9/14; A61K 9/20; A61K 9/22
(52) U.S. Cl. ........................ 424/484; 424/464; 424/468; 424/469; 424/473; 424/457
(58) Field of Search .................................. 424/484, 473, 424/457, 464, 468, 469

(56) References Cited

U.S. PATENT DOCUMENTS 6,120,803 A * 9/2000 Wong et al. ................. 424/473

* cited by examiner

Primary Examiner—Thurman K. Page
Assistant Examiner—Robert M. Joynes
(74) Attorney, Agent, or Firm—Townsend and Townsend and Crew, LLP

(57) ABSTRACT

The retention of oral drug dosage forms in the stomach is improved by using swellable dosage forms that are shaped in a manner that will prevent them from inadvertently passing through the pylorus as a result of being in a particular orientation. The planar projection of the shape is one that has two orthogonal axes of different lengths, the longer being short enough to permit easy swallowing prior to swelling while the shorter is long enough within one-half hour of swelling to prevent passage through the pylorus.

27 Claims, No Drawings

TABLET SHAPES TO ENHANCE GASTRIC RETENTION OF SWELLABLE CONTROLLED-RELEASE ORAL DOSAGE FORMS

BACKGROUND OF THE INVENTION

1. Field of the Invention

This invention is in the general field of pharmaceuticals, and relates in particular to formulations for drugs that benefit from a prolonged time of controlled release in the stomach and upper gastrointestinal (GI) tract, and from an enhanced opportunity for absorption in the stomach and upper GI tract rather than the lower portions of the GI tract. One goal of this invention is to release drugs in a controlled manner over an extended period of time. Another goal is to extend the time of delivery into the stomach of drugs that are preferentially absorbed high in the GI tract, and thereby to achieve a greater and more prolonged therapeutic effect with potentially diminished side effects. This will reduce the frequency of administration required and achieve a more efficient use of the drugs and a more effective treatment of local stomach disorders. A third goal is to minimize both lower-GI tract inactivation of the drug and drug effects on the lower intestinal flora.

2. Description of the Prior Art

Many drugs have their greatest therapeutic effect when released in the stomach, particularly when the release is prolonged in a continuous, controlled manner. Drugs delivered in this manner have a lower level of side effects and provide their therapeutic effects without the need for repeated dosages, or with a low dosage frequency. Localization of the drug delivery in the stomach is an advantage for the treatment of local disorders of the stomach such as esophageal reflux disease, for the eradication of ulcer-causing bacteria in the gastric mucosa, and for the treatment of disorders that require sustained antacid action. Sustained release in the stomach is also useful for therapeutic agents that the stomach does not readily absorb, since sustained release prolongs the contact time of the agent in the stomach or in the upper part of the small intestine, which is where absorption occurs and contact time is limited. Under normal or average conditions, for example, material passes through the small intestine in as little as 1 to 3 hours. For drugs that are absorbed almost exclusively in the small intestine, such as captopril and the cephalosporins, this short contact time limits the bioavailability of these drugs, particularly when the drugs are administered in a controlled-release dosage form.

The passage of matter through the stomach can be delayed in the normal digestive process by the physiological condition that is variously referred to as the digestive mode, the postprandial mode, or the "fed mode" (the latter term is used in the remainder of this specification for convenience). When the stomach is not in this mode, it is in the interdigestive or "fasting" mode. The difference between the two modes lies in the pattern of gastroduodenal motor activity.

In the fasting mode, the stomach exhibits a cyclic activity called the interdigestive migrating motor complex (IMMC). This activity occurs in four phases:

In Phase I, which lasts 45 to 60 minutes and is the most quiescent, few or no contractions occur.

In Phase II, irregular intermittent sweeping contractions occur that gradually increase in magnitude.

In Phase III, intense bursts of peristaltic waves appear in both the stomach and the small bowel. This lasts for 5 to 15 minutes.

Phase IV is a transition period of decreasing activity which lasts until the next cycle begins.

The total cycle time is approximately 90 minutes, and the contents of the stomach are swept out by the powerful peristaltic waves that occur during Phase III. Phase III of the IMMC thus functions as an intestinal housekeeper, sweeping swallowed saliva, gastric secretions, food particles, and particulate debris to the small intestine and colon, and preparing the upper tract for the next meal while preventing bacterial overgrowth. Pancreatic exocrine secretion of pancreatic peptide and motilin also cycle in synchrony with the motor pattern.

The fed mode is induced by nutritive elements immediately after food ingestion, and begins with a rapid and profound change in the motor pattern of the upper gastrointestinal (GI) tract, the change occurring over a period of 30 seconds to one minute. The change occurs almost simultaneously at all sites of the GI tract, before the stomach contents have reached the distal small intestine. Once the fed mode is established, the stomach generates 3–4 continuous and regular contractions per minute, similar to those of the fasting mode but with about half the amplitude. The pylorus is partially open, causing a sieving effect in which liquids and small particles flow continuously from the stomach into the intestine while indigestible particles greater in size than the pyloric opening are retropelled and retained in the stomach. This sieving effect thus causes the stomach to retain particles exceeding about 1 cm in size for approximately 4 to 6 hours.

The minimum particle size that will be retained in the stomach is thus substantially smaller in the fed mode than in the fasting mode. Particles large enough to be retained in the fasting mode are too large for practical administration in most patients. Particles of a smaller particle size can be retained in the stomach if they are administered to a patient who is in the fed mode, and this serves as an effective and feasible means of prolonging the residence time of these particles in the stomach.

Whether the subject is in the fed mode or the fasting mode, a further means of prolonging the residence time of particles in the stomach is to use particles that are initially small enough for comfortable ingestion but swell to a larger size upon contact with the gastric fluid in the stomach. The swelling can occur as a result of hydration of the particle material upon absorption of water from the gastric fluid, or as a result of gas generation, such as carbon dioxide for example, by contact of gastric fluid with the dosage form, the gas generation occurring in a membrane bag or otherwise within the dosage form. Swelling can also be achieved by placing a large tablet in a compressed condition under mechanical tension inside a small capsule which will release the tablet when the capsule contacts gastric fluid, permitting the released tablet to expand to its full relaxed size.

Disclosures of oral dosage forms that swell to sizes that will prolong the residence time in the stomach are found in U.S. Pat. No. 5,007,790 ("Sustained-Release Oral Drug Dosage Form;" Shell, inventor; Apr. 16, 1991), U.S. Pat. No. 5,582,837 ("Alkyl-Substituted Cellulose-Based Sustained-Release Oral Drug Dosage Forms;" Shell, inventor: Dec. 10, 1996): U.S. Pat. No. 5,972,389 ("Gastric-Retentive Oral Drug Dosage Forms for the Controlled Release of Sparingly Soluble Drugs and Insoluble Matter;" Shell et al., inventors; Oct. 26, 1999); International (PCT) Patent Application WO 98/55107 ("Gastric-Retentive Oral Drug Dosage Forms for Controlled Release of Highly Soluble Drugs;" Shell et al., inventors; publication date Dec. 10, 1998); and International (PCT) Patent Application WO 96/26718 ("Controlled Release Tablet;" Kim, inventor: publication date Sep. 6, 1996).

Even with swelling, a certain proportion of particles can pass through the pylorus regardless of whether the subject is in the fed mode or the fasting mode, if the particles become oriented when in the vicinity of the pylorus such that their longest dimension is in alignment with the pyloric axis. This is particularly true of tablets or caplets (cylindrical tablets with rounded ends) that are elongated in shape to facilitate swallowing. When dosage forms such as these swell due to imbibition of water, one dimension may achieve a length great enough to exceed the pyloric opening while the others may be significantly smaller. The dosage form will thus be retained in the stomach only if the form is oriented with the long dimension transverse to the pyloric opening. Accordingly, for a certain percentage of the administered units of these swellable forms, prolonged retention in the stomach is not achieved and the beneficial effect of the swelling is lost. There is thus only a limited assurance that the swelling will result in gastric retention of the dosage form.

SUMMARY OF THE INVENTION

It has now been discovered that by using a solid water-swellable dosage form of a particular shape, the proportion of these dosage forms that escapes through the pylorus due to a fortuitous orientation at the pylorus can be reduced or eliminated entirely while still having a dosage form that is easily swallowed. The shape that achieves this result is a non-circular and non-spherical shape which, when projected onto a planar surface, has two orthogonal axes of different lengths, the longer axis being at most 3.0 cm in length, preferably 2.5 cm or less in length, when the dosage form is in the unswollen state, and the shorter axis being long enough to achieve a length of at least 1.2 cm, preferably at least 1.3 cm, within the first one hour, and preferably thirty minutes of swelling time. In addition to enhancing gastric retention, the non-circular and non-spherical shape render the tablets of this invention convenient to swallow. The tablets are also smaller than many tablets of the prior art that were designed for a similar effect, and this offers an advantage for people who suffer from a psychological difficulty when attempting to swallow a tablet.

The improvement offered by this invention provides benefits to many types of drugs, including those whose activity is lessened for various reasons once they pass into regions of the gastrointestinal tract that are downstream of the stomach and upper regions of the small intestine, as well as those that give rise to detrimental physiological effects in these regions. These drugs range in solubility from those that are only sparingly soluble in water to those that are highly soluble.

The dosage form is a swellable body, preferably a polymeric matrix in which the drug is dispersed. The polymer is swellable upon imbibition of water and thus upon contact with gastric fluid when reaching the stomach. In certain embodiments of the invention, the polymer is erodible as well. When an erodible polymer is used, the polymer is one whose erosion rate is substantially slower than the swelling rate. In some cases, the erosion of the polymer is used as a means of releasing the drug to the stomach, and at times a combination of erosion and dissolution/diffusion is used.

In certain embodiments of this invention, the dosage form is a multilayered tablet in which one or more of the layers swells while the others do not. In further embodiments of the invention, the dosage form is a tablet with a core surrounded by a shell, and the core swells while the shell remains relatively dimensionally stable, or vice versa.

These and other features, characteristics, and embodiments of the invention will be apparent from the description that follows.

DETAILED DESCRIPTION OF THE INVENTION AND SPECIFIC EMBODIMENTS

Within the parameters stated above, the dosage forms of this invention, which will be referred to herein for convenience as "tablets" (although other forms are contemplated as well), may vary in shape. Some of the possible shapes are oval, triangle, almond, peanut, "bow tie," parallelogram, trapezoidal, pentagonal, and hexagonal, provided (as stated above) that the largest planar projection of the shape has at least two orthogonal dimensions, one being larger than the other. Preferred shapes are oval and parallelogram (notably diamond-shaped, i.e., a quadrilateral in which opposing sides are parallel and adjacent sides are not at right angles). In certain embodiments, the edges or corners of these shapes, particularly those of the parallelogram, are slightly rounded. Particularly preferred shapes are those that have three (orthogonal) planes of symmetry to aid in swallowing.

The tablet swells gradually upon immersion in water (and hence gastric fluid), and within one hour, and preferably thirty minutes of swelling time, the shorter axis of the table will have expanded to a length of 1.2 cm or more, and preferably 1.3 cm or more. This will reduce or eliminate the possibility that the tablet in its swollen state can pass through the pylorus when oriented with its long axis parallel to the axis of the pylorus, since the shorter axis dimension of at least 1.2 cm will then be transverse to the pyloric axis and will be large enough to resist passage through the pylorus. Prior to swelling of the tablet, the shorter axis may be as small as 0.7 cm in length, preferably 0.7 cm to 1.5 cm in length, and preferably 0.75 cm to 1.2 cm in length, and most preferably 0.8 cm to 1.0 cm in length. The longer of the two orthogonal axes will achieve a greater length when the tablet swells, but it should be small enough in the unswollen state to permit easy swallowing of the tablet. Accordingly, the longer orthogonal axis of the tablet-prior to swelling will be 3.0 cm or less in length, preferably 2.5 cm or less, and most preferably 1.5 cm to 2.5 cm. One example of a tablet that meets these descriptions is a diamond-shaped tablet (i.e., a tablet whose planar projection is a parallelogram with one diagonal dimension shorter than the other) in which the shorter diagonal is 0.9 cm and the longer diagonal is 1.5 cm. In this example, both of these dimensions are substantially greater than the thickness of the tablet.

Water-swellable polymers useful in the preparation of the dosage form of this invention include polymers that are non-toxic and that swell in a dimensionally unrestricted manner upon imbibition of water and hence of gastric fluid. Examples of polymers meeting this description are:

- cellulose polymers and their derivatives including, but not limited to, hydroxymethyl cellulose, hydroxyethyl cellulose, hydroxypropyl cellulose, hydroxypropylmethyl cellulose, carboxymethylcellulose, and microcrystalline cellulose
- polysaccharides and their derivatives
- polyalkylene oxides
- polyethylene glycols
- chitosan
- poly(vinyl alcohol)
- xanthan gum
- maleic anhydride copolymers
- poly(vinyl pyrrolidone)

starch and starch-based polymers maltodextrins poly (2-ethyl-2-oxazoline)

poly(ethyleneimine)

polyurethane hydrogels crosslinked polyacrylic acids and their derivatives

Further examples are copolymers of the polymers listed above, including block copolymers and graft polymers. Specific examples of copolymers are PLURONIC ® and TECTONICS®, which are polyethylene oxide-polypropylene oxide block copolymers available from BASF Corporation, Chemicals Div., Wyandotte, Mich., USA. Further examples are hydrolyzed starch polyacrylonitrile graft copolymers, commonly known as "Super Slurper" and available from Illinois Corn Growers Association, Bloomington, Ill., USA.

The term "cellulose" is used herein to denote a linear polymer of anhydroglucose. Preferred cellulosic polymers are alkyl-substituted cellulosic polymers that ultimately dissolve in the GI tract in a predictably delayed manner. Preferred alkyl-substituted cellulose derivatives are those substituted with alkyl groups of 1 to 3 carbon atoms each. In terms of their viscosities, one class of preferred alkyl-substituted celluloses are those whose viscosities are within the range of about 3 to about 110,000 centipoise as a 2% aqueous solution at 25° C. Another class are those whose viscosities are within the range of about 1,000 to about 5,000 centipoise as a 1% aqueous solution at 25° C. Particularly preferred alkyl-substituted celluloses are hydroxyethyl cellulose and hydroxypropyl methylcellulose. Presently preferred hydroxyethyl celluloses are NATRASOL® 250HX and 250HHX NF (National Formulary), available from Aqualon Company, Wilmington, Del., USA.

Of the polyalkylene oxides that are useful in the dosage forms of this invention, particularly preferred examples are poly(ethylene oxide) and poly(propylene oxide). Poly (ethylene oxide) is a linear polymer of unsubstituted ethylene oxide. Poly(ethylene oxide) polymers having viscosity-average molecular weights of about 200,000 and higher can be used. Examples of poly(ethylene oxide)s that are commercially available are:

POLYOX® NF, grade WSR Coagulant, molecular weight 5 million

POLYOX® grade WSR 301, molecular weight 4 million

POLYOX® grade WSR 303, molecular weight 7 million

POLYOX® grade WSR N-60K, molecular weight 2 million

All four are products of Union Carbide Chemicals and Plastics Company Inc. of Danbury, Conn., USA.

Polysaccharide gums may be either natural and modified (semi-synthetic). Examples are dextran, xanthan gum, gellan gum, welan gum and rhamsan gum. Xanthan gum is preferred. Alginates including, but not limited to, sodium and calcium alginates may also be used.

Of the crosslinked polyacrylic acids, the preferred types are those with a viscosity ranging from about 4,000 to about 40,000 centipoise for a 0.5% aqueous solution at 25° C. Three presently preferred examples are CARBOPOL® NF grades 971P, 974P and 934P (BFGoodrich Co., Specialty Polymers and Chemicals Div., Cleveland, Ohio, USA). Further examples are polymers known as WATER LOCK®, which are starch/acrylates/acrylamide copolymers available from Grain Processing Corporation, Muscatine, Iowa, USA.

For drugs of relatively high solubility, the preferred polymeric matrices are those with a relatively high molecular weight. With such a matrix, release of the drug is achieved by allowing the gastric fluid to diffuse into the matrix where the fluid dissolves the matrix-held drug and then diffuses outward while the matrix retains its integrity, or disintegrates at a rate that is considerably slower than the rate at which the drug is dissolved from the matrix. Controlled release is thus achieved by the integrity of the matrix and the need for the gastric fluid to diffuse into the matrix to reach the drug. For drugs of relatively low solubility, preferred polymeric matrices are those that erode while the drug is being released since diffusion and dissolution occur too slowly for an effective drug release rate and the erosion adds to the release rate. Controlled release is thus achieved at least in part by the controlled rate of erosion of the matrix, and the need for the matrix to erode in order to release much of the drug.

For poly(ethylene oxide) matrices, those that are preferred for relatively high-solubility drugs are those with viscosity-average molecular weights ranging from about 2,000,000 to about 7,000,000, and preferably from about 4,000,000 to about 7,000,000. For drugs of relatively low solubility, the preferred poly(ethylene oxide)s are those with viscosity-average molecular weights ranging from about 200,000 to about 2,000,000. A preferred viscosity range is about 50 to about 100,000 centipoise for a 2% aqueous solution at 25° C.

Drugs of relatively high solubility are generally considered to be those whose solubility in water at 37° C. is greater than one part by weight of the drug in twenty parts by weight of water. An alternative and preferred definition is those drugs whose solubility in water at 37° C. is greater than one part by weight of the drug in ten parts by weight of water, and a further alternative and even more preferred definition is those drugs whose solubility in water at 37° C. is greater than one part by weight of the drug in three parts by weight of water. Drugs of relatively low solubility are generally considered to be those whose solubility in water at 37° C. is from about 0.005% to about 10% by weight, and preferably those whose solubility in water at 37° C. is from about 0.01% to about 5% by weight.

Tablets in accordance with this invention can be prepared by conventional techniques, including common tabletting methods. These methods involve mixing, comminution, and fabrication steps commonly practiced by and well known to those skilled in the art of manufacturing drug formulations. Examples of such techniques are:

(1) Direct compression using appropriate punches and dies, such as those available from Elizabeth Carbide Die Company, Inc., McKeesport, Pa., USA. The punches and dies are fitted to a suitable rotary tabletting press, such as the Elizabeth-Hata single-sided Hata Auto Press machine, with either 15, 18 or 22 stations, and available from Elizabeth-Hata International, Inc., North Huntington, Pa., USA.;

(2) Injection or compression molding using suitable molds fitted to a compression unit, such as those available from Cincinnati Milacron, Plastics Machinery Division, Batavia, Ohio, USA.;

(3) Granulation such as, but not limited to, fluid bed or high shear granulation or roller compaction, followed by compression; and (4) Extrusion of a paste into a mold or to an extrudate to be cut into lengths.

When tablets are made by direct compression, the addition of lubricants may be helpful and is sometimes important to promote powder flow and to prevent capping of the tablet (the breaking off of a portion of the tablet) when the pressure is relieved. Useful lubricants are magnesium stearate (in a concentration of from 0.25% to 3% by weight, preferably about 1% or less by weight, in the powder mix), and hydrogenated vegetable oil (preferably hydrogenated and refined triglycerides of stearic and palmitic acids at about 1% to 5% by weight, most preferably about 2% by weight). Additional excipients may be added to enhance powder flowability, tablet hardness, and tablet friability and to reduce adherence to the die wall.

As indicated above, the dosage forms of the present invention find utility when administered to subjects who are either in the fed mode or the fasting mode. Administration during the fed mode is preferred, since the narrowing of the pyloric opening that occurs in the fed mode serves as a further means of promoting gastric retention by retaining a broader range of smaller dosage form sizes. The patterns of gastroduodenal motor activity that distinguish the two modes from each other are described above.

The fed mode is normally induced by food ingestion, but can also be induced pharmacologically by the administration of pharmacological agents that have an effect that is the same or similar to that of a meal. These fed-mode inducing agents may be administered separately or they may be included in the dosage form as an ingredient dispersed in the dosage form or in an outer immediate release coating. Examples of pharmacological fed-mode inducing agents are disclosed in co-pending U.S. patent application Ser. No. 09/432,881, filed Nov. 2, 1999, entitled "Pharmacological Inducement of the Fed Mode for Enhanced Drug Administration to the Stomach," inventors Markey, Shell, and Berner, the contents of which are incorporated herein by reference.

The drug that is contained in the dosage form for controlled release may be any chemical compound, complex or composition that is suitable for oral administration and that has a beneficial biological effect, preferably a therapeutic effect in the treatment of a disease or an abnormal physiological condition. Examples of relatively high solubility drugs to which this invention is applicable are metformin hydrochloride, vancomycin hydrochloride, captopril, lisinopril, erythromycin lactobionate, ranitidine hydrochloride, sertraline hydrochloride, ticlopidine hydrochloride, baclofen, amoxicillin, cefuroxime axetil, cefaclor, clindamycin, levodopa, doxifluridine, tramadol, fluoxitine hydrochloride, bupropion, potassium chloride, and esters of ampicillin. Examples low solubility drugs to which this invention is applicable are saguinavir, ritonavir, nelfinavir, thiamphenicol, ciprofloxacin, calcium carbonate, clarithromycin, azithromycin, ceftazidime, acyclovir, ganciclovir, cyclosporin, digoxin, paclitaxel, iron salts, topiramate, and ketoconazole. Other drugs suitable for use and meeting the solubility criteria described above will be apparent to those skilled in the art. This invention is of particular interest for antibiotics in general. This invention is also of particular interest for angiotensin converting inhibitors, particularly lisinopril, enalapril, captopril, and benazepril. A particularly preferred group of drugs is lisinopril, acyclovir, metformin hydrochloride, baclofen, ciprofloxacin, furosemide, cyclosporin, sertraline hydrochloride, and calcium carbonate.

The invention is also of use with drugs that have been formulated to include additives that impart a small degree of hydrophobic character to further retard the release rate of the drug into the gastric fluid. One example of such a release rate retardant is glyceryl monostearate. Other examples are fatty acids and salts of fatty acids, one example of which is sodium myristate. The quantities of these additives when present can vary; and in most cases, the weight ratio of additive to drug will range from about 1:20 to about 1:1, and preferably from about 1:8 to about 1:2.

In some embodiments of this invention, the dosage form may contain an additional amount of the drug in a quickly dissolving coating on the outer surface of the dosage form. This coating is referred to as a "loading dose" and its purpose is to provide immediate release into the patient's bloodstream upon ingestion of the dosage form without first requiring the drug to diffuse through the polymer matrix. An optimal loading dose is one that is high enough to quickly raise the blood concentration of the drug but not high enough to produce the transient overdosing that is characteristic of highly soluble drugs that are not administered in controlled-release formulations.

A film coating may also be included on the outer surface of the dosage form for reasons other than a loading dose. The coating may thus serve an aesthetic function or a protective finction, or it may make the dosage form easier to swallow or mask the taste of the drug.

The drug loading in the dosage form is not critical to this invention and may vary widely, although the choice of drug loading will affect the release rate and in some cases the release rate profile over time. In most cases, the drug constitutes from about 1% to about 98% by weight of the dosage form. In preferred embodiments, the drug constitutes from about 5% to about 95% by weight of the dosage form, and in the most preferred embodiments, the drug constitutes from about 50% to about 93% by weight of the dosage form. For drugs that are highly potent and therefore administered in small amounts, the drug loading as a percent of the tablet weight may be considerably lower since the tablet must be large enough to meet the size limitations of this invention in order to achieve gastric retention.

As stated above, the tablet shapes of the present invention offer various types of advantages to orally administered drugs, all stemming from the improved retention of the dosage form in the stomach. Depending on the particular drugs, these advantages include both improvements in the bioavailability and pharmacological efficacy of the drug and the lessening of side effects. In many cases, the passage of a drug from the stomach into the small intestine while the drug is still in a tablet or other dosage form results in lowering the therapeutic efficacy of the drug, either because the small intestine lacks the favorable conditions that exist in the stomach, or because of unfavorable conditions in the colon, or both.

For example, most orally administered antibiotics are capable of altering the normal flora of the gastrointestinal tract, and particularly the flora of the colon. One result of these alterations is the overgrowth of *Clostridium difficile*, an organism that releases dangerous toxins. An increase in the level of these toxins can cause pseudomembranous colitis, which has been reported as a side effect of many antibiotics that occurs when they pass from the stomach to the small intestine. In its milder forms pseudomembranous colitis can cause mild nausea and diarrhea, while in its stronger forms it can be life-threatening or fatal. Examples of antibiotics that pose this type of threat are amoxicillin, cefuroxime axetil, and clindamycin. Cefuroxime axetil (i.e., the axetil ester of cefuroxime), for example, becomes active when hydrolyzed to free cefuroxime, and when this occurs prior to absorption, damage to essential bacterial flora can occur. Hydrolysis to the active form typically occurs in the tissues into which the ester has been absorbed, but if the ester reaches the lower intestine, enzymes in the lower intestine cause the hydrolysis to occur in the intestine itself, which not only renders the drug incapable of absorption but also converts the drug to the form that can alter the flora. Further examples are clarithromycin, azithromycin, cefiazidime, ciprofloxacin, and cefaclor. Use of the tablet shapes of the present invention helps to avoid this antibiotic-induced overgrowth of the lower intestinal flora by helping to restrict the delivery of antibiotics, regardless of their level of solubility, to the stomach and upper small intestine.

Another class of drugs that benefit from the tablet shapes of this invention are those that are absorbed only in the upper GI tract but suffer from incomplete absorption or from wide differences in absorption, both within a single patient and between different patients. One example of such a drug is cyclosporine, a drug of low solubility that is used as an immunosuppressant to reduce organ rejection in transplant surgery. In addition to its low solubility, cyclosporine has a low absorption rate of about 30% on average, together with wide absorption variability ranging from as little as 5% in some patients to as much as 98% in others. The variability is attributable in part to differences among the various disease states existing in the patients to whom the drug is administered, and in part to differences in the length of time between the transplant surgery and the administration of the drug. The variability can also be attributed however to differences in the length of time required for intestinal transit between the stomach and the colon and in the possibility of a proportion of the tablets passing through the pylorus due to fortuitous tablet orientation. These differences can be lessened by the use of the tablet shapes of this invention.

Another class of drugs that will benefit from this invention are drugs that are susceptible to degradation by intestinal enzymes. The degradation occurs before the drug can be absorbed through the intestinal wall, leaving only a fraction of the administered dose available for the intended therapeutic action. An example of such a drug is the pro-drug doxifluridine (5'-deoxy-5-fluouridine (dFUR)). The activity of this pro-drug depends on its activation to 5-fluorouracil by pyrimidine nucleoside phosphorylases. These enzymes are found in tumors as well as in normal tissues, and their activity in tumor cells is more than twice their activity in normal tissue. In addition, these enzymes demonstrate their highest activity in the large intestine. When doxifluridine is administered orally, there is a risk that it will be converted to 5-fluorouracil in the intestine before it reaches the tumors. 5-Fluorouracil is much more toxic than doxifluridine and causes nausea and diarrhea and severe damage to the intestinal villi. Other drugs that can produce a similar effect upon reaching the colon are cyclosporine and digoxin. These effects can be lessened by use of the tablet shapes of this invention.

A further class of drugs whose effectiveness declines when the drugs are allowed to pass into the large intestine are those that are susceptible to inactivation by drug transporters that reside in lower gastrointestinal tract enterocytes. The inactivation occurs before the drug penetrates the intestinal wall, leaving only a fraction of the administered dose available for the intended therapeutic action. One example of a drug transporter is the p-glycoprotein efflux system, in which a p-glycoprotein acts as an absorption barrier to certain drugs that are substrates for the p-glycoprotein. The barrier acts by attaching to these drugs and transporting them drug back into the lumen, e.g., the duodenum, jejunum/ileum or colon, from which they were absorbed, or by preventing them from being absorbed at all. This restriction of the drug to the interior of the GI tract is effectively an inactivation of the drug since the drug must pass out of the GI tract into the bloodstream to be effective. Thus, while the p-glycoprotein efflux system is useful in many respects, such as preventing toxic compounds from entering the brain, it interferes with the efficacy of certain drugs whose absorption is necessary in achieving the therapeutic effect. The p-glycoprotein concentration is lowest in the stomach and increases in concentration down the GI tract to the colon where the p-glycoprotein is most prevalent. Cyclosporine is an example of a drug of low solubility that is susceptible to inactivation by the p-glycoprotein efflux system, in addition to its susceptibility to degradation by colonic bacterial enzymes. Other examples of drugs that are susceptible to the p-glycoprotein efflux system are the anti-cancer drug paclitaxel, ciprofloxacin, and the HIV protease inhibitors saquinavir, ritonavir, and nelfinavir. Because of the p-glycoprotein efflux system, these drugs benefit from the tablet shapes of the present invention by raising the probability that the drugs will be released into the upper GI tract where p-glycoprotein is lowest.

A still further class of drugs that benefit from the present invention are those that require an acidic environment for effective bioavailability. For certain drugs, the pH at a given site within the GI tract is an essential determinant of the bioavailability of the drug, since the solubility of the drug varies with pH. The stomach has a low pH and thus creates an acidic environment, while the small intestine has a higher pH, creating a slightly acidic to alkaline environment. Some drugs achieve bioavailability only when ionized by the acidic environment of the stomach. Other drugs are more bioavailable in a non-ionized state. Acidic drugs that have a low pK, for example, are in the neutral form in the stomach, and those that are more bioavailable in this state are preferentially absorbed in the stomach or upper duodenum. Examples of highly soluble drugs that meet this description are esters of ampicillin. Examples of low solubility drugs that behave similarly are iron salts, digoxin, ketoconazole, fluconazole, griseofulvin, itraconazole, and micoconazole. Iron salts are used in the treatment of the various forms of anemia, digoxin is used in the treatment of heart disease, and ketoconazole is used in the treatment of systemic fungal infections such as candidiasis, canduria, blastomycosis, coccidiomycosis, histoplasmosis, chronomycosis, and paco-coccidiomycosis. Still further drugs that are more absorbable in the neutral form that is maintained at low pH are those whose molecular structure contains at least one group that becomes ionized in the pH range of 5 through 8, which is the pH range encountered in the small intestine and the region of the colonic junction. Zwitterionic drugs that are more readily absorbed when in a charged form are another example, particularly when the charged form is achieved only when the drug is in the acidic environment of the stomach or the duodenal cap. The bioavailability of all of these drugs can be maximized by lowering the probability that they will pass through the pylorus due to a fortuitous orientation of the dosage form.

A still further group of drugs that benefit from the tablet shapes of the present invention are those that are absorbed in the duodenum and jejunum, but are not well absorbed from the colon.

A still further group of drugs that benefit from the tablet shapes of the present invention are those that are soluble in an acidic environment but insoluble in an alkaline or neutral environment. The HIV protease inhibitor nelfinavir mesylate is one example of such a drug. Portions of the drug that are undissolved cannot be absorbed. Portions that are dissolved but not yet absorbed when they pass from the stomach into the small intestine may undergo precipitation and loss of their therapeutic benefit. This is confirmed by the fact that the presence of food in the GI tract substantially increases the absorption of orally administered nelfinavir. Peak plasma concentration and area under the plasma concentration-time curve of nelfinavir are two to three times greater when doses are administered with or following a meal. This is believed to be due at least in part to enhanced retention of the drug in the stomach.

The foregoing is offered primarily for purposes of illustration. It will be readily apparent to those skilled in the art that further drugs can be included, and that the shapes, components, additives, proportions, methods of formulation, and other parameters described herein can be modified further or substituted in various ways without departing from the spirit and scope of the invention.

What is claimed is:

1. A controlled-release oral drug dosage form for releasing a drug into at least a portion of a region defined by the stomach and the upper gastrointestinal tract, said dosage form comprising a solid monolithic matrix with said drug contained therein, said matrix being non-circular in shape and having first and second orthogonal axes of unequal length, said matrix being one that swells in an unrestricted manner along both such axes upon imbibition of water, the longer such axis having a maximum length of 3.0 cm when said matrix is unswollen, and the shorter such axis achieving a minimum length of 1.2 cm within one hour of immersion of said dosage form in water and wherein said matrix has a shape which when projected onto a plane, is either an oval or a parallelogram.

2. A controlled-release oral drug dosage form in accordance with claim 1 in which said shorter axis achieves a minimum length of 1.2 cm within thirty minutes of immersion of said dosage form in water.

3. A controlled-release oral drug dosage form in accordance with claim 1 in which said shorter axis achieves a minimum length of 1.3 cm within one hour of immersion of said dosage form in water.

4. A controlled-release oral drug dosage form in accordance with claim 1 in which said shorter axis achieves a minimum length of 1.3 cm within thirty minutes of immersion of said dosage form in water.

5. A controlled-release oral drug dosage form in accordance with claim 1 in which said shorter axis ha s a length of 0.7 cm to 1.5 cm when said matrix is unswollen.

6. A controlled-release oral drug dosage formn in accordance with claim 1 in Which said shorter axis has a length of 0.75 cm to 1.2 cm when said matrix is unswollen.

7. A controlled-release oral drug dosage form in accordance with claim 1 in which said shorter axis has a length of 0.8 cm to 1.0 cm when said matrix is unswollen.

8. A controlled-release oral drug dosage form in accordance with claim in which said longer axis has a maximum length of 2.5 cm when said matrix is unswollen.

9. A controlled-release oral drug dosage form in accordance with claim 1 in which said longer axis has a length of 1.5 cm to 2.5 cm when said matrix is unswollen.

10. A controlled-release oral drug dosage form in accordance with claim 1 in which said matrix is a water-swellable polymer.

11. A controlled-release oral drug dosage form in accordance with claim 10 in which said water-swellable polymer is a member selected from the group consisting of poly (ethylene oxide), poly(vinyl alcohol), cellulose, alkyl-substituted cellulose, hydroxyalkyl-substituted cellulose, crosslinked polyacrylic acids, and xanthan gum.

12. A controlled-release oral drug dosage form in accordance with claim 10 in which said water-swellable polymer is a member selected from the group consisting of poly (ethylene oxide), poly(vinyl alcohol), hydroxymethyl cellulose, hydroxyethyl cellulose, hydroxypropyl cellulose, hydroxypropylmethyl cellulose, and carboxymethyl cellulose.

13. A controlled-release oral drug dosage form in accordance with claim 10 in which said water-swellable polymer is a member selected from the group consisting of poly (ethylene oxide), hydroxypropylmethyl cellulose, and hydroxyethyl cellulose.

14. A controlled-release oral drug dosage form in accordance with claim 10 in which said water-swellable polymer is poly(ethylene oxide).

15. A controlled release oral drug dosage form in accordance with claim 1 in which said drug has a solubility in water at 37° C. that is at least one part by weight of said drug in twenty parts by weight of water, and said matrix is a poly(ethylene oxide) having a viscosity-average molecular weight within the range of about 2,000,000 to about 7,000,000.

16. A controlled release oral drug dosage form in accordance with claim 1 in which said drug has a solubility in water at 37° C. that is at least one part by weight of said drug in tenaparts by weight of water, and said matrix is a poly(ethylene oxide) having a viscosity-average molecular weight within the range of about 2,000,000 to about 7,000,000.

17. A controlled release oral drug dosage form in accordance with claim 1 in which said drug has a solubility in water at 37° C. that is at least one part by weight of said drug in three parts by weight of water, and said matrix is a poly(ethylene oxide) having a viscosity-average molecular weight within the range of about 2,000,000 to about 7,000,000.

18. A controlled release oral drug dosage form in accordance with claim 1 in which-said drug has a solubility in water at 37° C. that is from about 0.005% to about 10% by weight, and said matrix is a poly(ethylene oxide) having a vis sity-average molecular weight within the range of about 200,000 to about 2,000,000.

19. A controlled-release oral drug dosage form in accordance with claim 1 in which said drug has a solubility in water at 37° C. that is from about 0.01% to about 5% by weight, and said matrix is a poly(ethylene oxide) having a viscosity-average molecular weight within the range of about 200,000 to about 2,000,000.

20. A controlled-release oral drug dosage form in accordance with claim 1 in which said drug is a member selected from the group consisting of lisinopril, acyclovir, rhetformin hydrochloride, baclofen, ciprofloxacin, furosemide, cyclosporin, sertraline hydrochloride, and calcium carbonate.

21. A controlled-release oral drug dosage form in accordance with claim 1 in which said drug is an antibiotic.

22. A controlled-release oral drug dosage form in accordance with claim 1 in which said drug is an angiotensin converting inhibitor.

23. A controlled-release oral drug dosage form in accordance with claim 22 in which said angiotensin converting inhibitor is a member selected from the group consisting of lisinopril, enalapril, captopril, and benazepril.

24. A controlled-release oral drug dosage form in accordance with claim 1 in which said drug is acyclovir.

25. A controlled-release oral drug dosage form in accordance with claim 1 in which said drug is metformin hydrochloride.

26. A controlled-release oral drug dosage form in accordance with claim 1 in which said drug is baclofen.

27. A controlled-release oral drug dosage form in accordance with claim 1 in which said drug is ciprofloxacin.

* * * * *

UNITED STATES PATENT AND TRADEMARK OFFICE
CERTIFICATE OF CORRECTION

PATENT NO.        : 6,488,962 B1                                      Page 1 of 1
APPLICATION NO. : 09/598061
DATED             : December 3, 2002
INVENTOR(S)       : Bret Berner and Jenny Louie-Helm It is certified that error appears in the above-identified patent and that said Letters Patent is hereby corrected as shown below:

Column 11, line 17 "comprising" should be changed to --consisting essentially of--.

Column 12, line 44 "rhetformin" should be changed to --metformin--.

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,488,962 B1 | Page 1 of 1 |
| APPLICATION NO. | : 09/598061 | |
| DATED | : December 3, 2002 | |
| INVENTOR(S) | : Brent Berner and Jenny Louie-helm | |

It is certified that error appears in the above-identified patent and that said Letters Patent is hereby corrected as shown below:

Column 11, line 41 (Claim 8, line 2) thereof: change "claim in which said longer axis" to --claim 1 in which said longer axis--

Signed and Sealed this

Seventeenth Day of January, 2012

David J. Kappos
*Director of the United States Patent and Trademark Office*